US009518114B2

(12) United States Patent
Aguilar et al.

(10) Patent No.: US 9,518,114 B2
(45) Date of Patent: Dec. 13, 2016

(54) TREATING BLADDER TUMOR CELLS USING FIBRONECTIN ATTACHMENT PROTEIN AS A TARGET

(75) Inventors: Ruben Claudio Aguilar, West Lafayette, IN (US); Timothy Ratliff, West Lafayette, IN (US); David Thompson, West Lafayette, IN (US); Scott Crist, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 406 days.

(21) Appl. No.: 13/884,427

(22) PCT Filed: Nov. 11, 2011

(86) PCT No.: PCT/US2011/060339
§ 371 (c)(1),
(2), (4) Date: May 9, 2013

(87) PCT Pub. No.: WO2012/065044
PCT Pub. Date: May 18, 2012

(65) Prior Publication Data
US 2013/0230584 A1 Sep. 5, 2013

Related U.S. Application Data

(60) Provisional application No. 61/412,973, filed on Nov. 12, 2010.

(51) Int. Cl.
*C07K 16/12* (2006.01)
*C07K 16/28* (2006.01)
*C07K 16/30* (2006.01)
*A61K 39/00* (2006.01)

(52) U.S. Cl.
CPC .............. *C07K 16/28* (2013.01); *C07K 16/12* (2013.01); *C07K 16/1278* (2013.01); *C07K 16/3038* (2013.01); *A61K 2039/505* (2013.01)

(58) Field of Classification Search
None
See application file for complete search history.

(56) References Cited

U.S. PATENT DOCUMENTS

| 5,013,556 A | 5/1991 | Woodle et al. |
| 5,395,619 A | 3/1995 | Zalipsky et al. |
| 5,618,916 A * | 4/1997 | Ratliff .................... C07K 14/35 424/130.1 |
| 5,631,018 A | 5/1997 | Zalipsky et al. |

FOREIGN PATENT DOCUMENTS

WO    WO98/07409    2/1998

OTHER PUBLICATIONS

Zhao et al., Int. J. Cancer, 2000, 86(1), 83-88.*
Sy et al., Biomaterials, Jun. 2010, 31(18), 4987-94.*
PCT Search Report and Written Opinion for PCT/US2011/060339, completed Jun. 12, 2012.
Zhao, Weicheng, et al., "Role of a Bacillus Calmette-Guerin Fibronectin Attachment Protein in BCG-Induced Antitumor Activity", 2000, Int. J. Cancer, No. 86, pp. 83-88.
Sy, Jay C., et al., "Surface Functionalization of Polyketal microparticles with Nitrilotriacetic Acid-Nickel Complexes for Efficient Protein Capture and Delivery", Jun. 2010, Biomaterials, vol. 31, No. 18, pp. 4987-4994.
Coon, Brian G., et al., "Fibronection Attachment Protein From Bacillus Calmette-Guerin as Targeting Agent for Bladder Tumor Cells", 2011, Int. J. Cancer, No. 00, pp. 000-000.
Verbelen, Claire, et al., "Direct Measurement of *Mycobacterium-Fibronection* Interactions", 2009, Integr. Biol., No. 1, pp. 296-300.

* cited by examiner

*Primary Examiner* — James H Alstrum Acevedo
*Assistant Examiner* — Roy Teller
(74) *Attorney, Agent, or Firm* — Reichel Stohry LLP; Natalie J. Dean; Mark C. Reichel

(57) ABSTRACT

Composition and methods are disclosed for utilizing micro-aggregation of FAP-containing complexes to promote their fast internalization. This approach allows the uptake of cytotoxic cargo coupled to either FAP-Antibodies or FAP-liposome complexes by tumor bladder cells. Importantly, this approach is efficient even under serum-free conditions such as the ones found in the lumen of the bladder.

20 Claims, 10 Drawing Sheets

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Arg Trp Phe Val
1
```

TREATING BLADDER TUMOR CELLS USING FIBRONECTIN ATTACHMENT PROTEIN AS A TARGET

CROSS REFERENCE TO RELATED APPLICATIONS

This application is a national stage entry under 35 USC §371(b) of International Application No. PCT/US2011/060339, filed Nov. 11, 2011, which claims priority under 35 USC §119(e) to U.S. provisional application Ser. No. 61/412,973 filed on Nov. 12, 2010, the entire disclosures of which are incorporated herein by reference.

BACKGROUND

Bladder cancer is the fourth most common cancer in men and eleventh most common in women. Approximately 80% of the cases are classified as superficial cancer and most are treated with surgery alone. However, 70% of newly diagnosed patients suffer disease recurrence after surgical treatment. Therefore, the development of efficient therapeutic countermeasures against this pathology is a high priority.

The bladder displays unique characteristics and challenges as an organ to be targeted for therapy. Specifically, bladder epithelial cells lining the luminal surface, known as umbrella cells, are engaged in tight junctions that prevent access to the lower transitional cell layers. Furthermore, umbrella cells express characteristic extracellular proteins (uroplakins) that assemble into semi-rigid plaques that effectively shield the apical surface. The urothelium is further isolated from the bladder lumen by a mucin layer comprised of GlycosAminoGlycans (GAG) that are produced and assembled on the apical surface of the umbrella cells. In addition, the well-differentiated umbrella cells have limited secretory and endocytic capacity. In contrast, malignant bladder cells are usually less differentiated and polarized, exhibit diminished uroplakin expression and low GAG layer synthesis. Therefore, as opposed to normal bladder epithelia, neoplastic cells are exposed to the lumen of the bladder. This leads to increased accessibility of tumor lesions to therapeutic agents, compared to the well-protected normal regions of the bladder. However, constant urine influx and periodic voiding of the bladder makes the direct instillation of therapeutic drugs limited in their impact on bladder tumor cells.

At present, intravesical instillation of live *Mycobacterium bovis* bacillus Calmette-Guerin (BCG) is currently the adjuvant therapy of choice for the treatment of superficial bladder tumors. While the specific mechanisms of BCG-mediated antitumor activity is not yet fully understood, direct targeting and binding to bladder tumor cells, followed by cellular uptake and subsequent activation of adaptive immune responses, are required. Nevertheless, intravesical BCG is associated with high local morbidity and a risk of systemic mycobacterial infection. Notably, multiple instillations leads to increased toxicity, thus limiting patient tolerance for the treatment regimen required for effective anti-cancer activity. Therefore, the development of high-affinity, non-toxic targeting strategies is of high priority in the field.

A breakthrough came from the identification of BCG's Fibronectin Attachment Protein (FAP) as the targeting molecule used by the bacteria to adhere to bladder tumor cells (Ratliff et al. *Infect Immun* 1993; 61: 1889-94; Schorey et al. *Mol Microbiol* 1996; 21: 321-9; and Schorey et al. *Infect Immun* 1995; 63: 2652-7). FAP was shown to interact with $\alpha_5\beta_1$ Integrin-bound fibronectin (FBN) and undergo internalization by tumor cells. Since FAP by itself was observed to mediate antitumor activity in FAP-immune mice (Sinn et al. *Cancer Immunol Immunother* 2008; 57: 573-9), it may represent a lower-risk alternative to BCG for therapeutic purposes. In addition, the internalization of FAP by bladder tumor cells provides a novel and potentially powerful approach for the delivery of therapeutics that may greatly enhance the antitumor effect of FAP.

In accordance with the present disclosure a FAP-targeted delivery strategy is provided for delivering and inducing the uptake of cytotoxic agents into bladder tumor cells.

SUMMARY

In accordance with one embodiment, a polyvalent complex is provided wherein the complex is polyvalent for the fibronectin attachment protein (FAP). Applicants have discovered that FAP's low internalization rate by bladder tumor cells can be enhanced by micro-aggregation of the FAP/FBN complexes, using compounds multivalent for FAP. Such complexes will be selectively taken up by bladder cancer cells at an enhanced rate. The multivalent complexes comprising functional fibronectin attachment proteins bind to fibronectin and are taken up by bladder cancer cells. In one embodiment these complexes are used to inhibit cell proliferation and to induce apoptosis. As used herein a functional FAP may be the native protein, a FAP fragment or a FAP variant having one or more modifications (insertion, deletion, substitution of one or more amino acids) in the FAP protein sequence, or a recombinant fusion protein derivative of FAP, wherein the peptide is capable of binding to fibronectin and being taken up by bladder cancer cells. In one embodiment the functional FAP comprises the RWFV sequence (residues 213-216) of the native peptide. In one embodiment the complex further comprises a diagnostic agent or therapeutic agent.

BRIEF DESCRIPTION OF THE DRAWINGS

FIG. 1A is a schematic representation of an antibody-induced FAP micro-aggregation strategy for enhancing uptake of FAP by bladder tumor cells. FIG. 1B. is a schematic representation of the fusogenic effects of Rab5 dominant positive (Q79L) on the endosomal compartments, resulting in the accumulation of the FAP complexes (represented by an *) in the endosome (E) and not being further processed by the lysozyme (L).

FIG. 2A is a graph demonstrating the results of incubating T24 bladder tumor cells with 10 μM His$_6$-FAP for 1 h at 37° C. and after a wash step, incubating the washed cells with either α-HA or α-FAP polyclonal antibodies at the indicated dilutions. FAP-associated fluorescence was quantified and results were represented as box-plots. FIG. 2B is a graphic representation of the internalization of the FAP after incubation for the indicated times. FAP-associated fluorescence was quantified. FAU: Fluorescence Arbitrary Units.

FIG. 3A is a graph demonstrating the results of incubating T24 bladder cells with siRNA against clathrin and its ability to inhibit FAP internalization. Transferrin ("Tf", was used as a clathrin-dependent cargo control) and FAP-associated fluorescence was quantified. Results are expressed as a fraction with respect to the control (i.e., no siRNA), and as indicated in the left panel of FIG. 3A siRNA against clathrin failed to inhibit FAP internalization. FIG. 3B is a graph demonstrating the results of incubating T24 bladder cells with siRNA against caveolin-1 and its ability to inhibit FAP internalization. As indicated in the left panel of FIG. 3B siRNA against caveolin-1 inhibited FAP internalization (but as expected, failed to inhibit transferrin uptake, see right panel of FIG. 3B). FIG. 3C is a photograph of a Western blot demonstrating cells treated with the indicated siRNAs (Cav1: Caveolin-1; Chc: Clathrin heavy chain) effectively reduced the respective Clathrin and Caveolin-1 protein levels in the cells. Tubulin was used as a loading control.

FIG. 4 is a graphic representation of the amount of FAP-Lamp2 co localizing puncta as a function of incubation time.

FIG. 6 shows that FAP-associated fluorescence remained bound to the cells after long incubations under acidic conditions.

DETAILED DESCRIPTION

Definitions

Figure 1A:
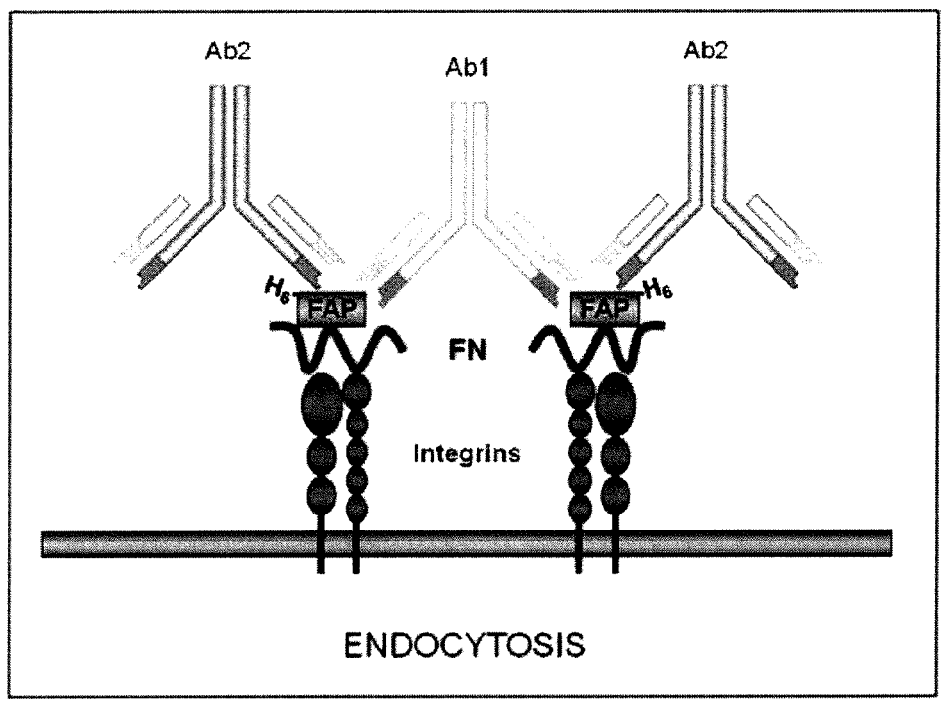
FIG. 1A-1B. T24 Bladder Tumor cells internalize Antibody-crosslinked FAP-AlexaFluor647 into Rab5$^{Q79L}$-GFP labeled compartments.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) *J. Mol. Biol.* 215:403-410) are available for determining sequence identity.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating a tumor" will refer in general to maintaining or reducing the tumor size or eliminating detectable cancer cells from the patient undergoing treatment.

As used herein an "effective" amount or a "therapeutically effective amount" of a therapeutic agent refers to a nontoxic but sufficient amount of an agent to provide the desired effect. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

As used herein an amino acid "substitution" refers to the replacement of one amino acid residue by a different amino acid residue.

As used herein, the term "conservative amino acid substitution" is defined herein as exchanges within one of the following five groups:
I. Small aliphatic, nonpolar or slightly polar residues:
Ala, Ser, Thr, Pro, Gly;
II. Polar, negatively charged residues and their amides:
Asp, Asn, Glu, Gln, cysteic acid and homocysteic acid;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine As used herein the general term "polyethylene glycol" or "PEG", refers to mixtures of condensation polymers of ethylene oxide and water, in a branched or straight chain, represented by the general formula $H(OCH_2CH_2)$—OH, wherein n is at least 9. Absent any further characterization, the term is intended to include polymers of ethylene glycol with an average total molecular weight selected from the range of 500 to 40,000 Daltons. "polyethylene glycol" or "PEG" is used in combination with a numeric suffix to indicate the approximate average molecular weight thereof. For example, PEG-5,000 refers to polyethylene glycol having a total molecular weight average of about 5,000.

As used herein the term "pegylated" and like terms refers to a compound that has been modified from its native state by linking a polyethylene glycol polymer to the compound. A "pegylated glucagon peptide" is a glucagon peptide that has a PEG chain covalently bound to the glucagon peptide.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein, the term "antibody" refers to a polyclonal or monoclonal antibody or a binding fragment thereof such as Fab, $F(ab')_2$ and Fv fragments that specifically binds to an antigenic site.

As used herein the term "patient" without further designation is intended to encompass any warm blooded vertebrate domesticated animal (including for example, but not limited to livestock, horses, cats, dogs and other pets) and humans.

As used herein the term "cancer patient" is intended to encompass any patient that has been diagnosed with benign or malignant neoplastic cells, or was at one time diagnosed with benign or malignant neoplastic cells and continues to receive treatments related to their cancer. This includes patients with active cancers, those in remission, and patients who have been subsequently deemed cancer free but continue to receive treatment for their cancer. For example breast cancer or ovarian cancer patients may continue to receive aromatase therapy for their cancers long after cancer cells can no longer be detected in their bodies.

A "fibronectin attachment protein" as used herein includes the native fibronectin attachment protein of *Mycobacterium bovis* Bacillus* Calmette-Guérin, as well as any derivative (including amino acid substitutions or additions, or post translational modifications, e.g. methylation, acylation, ubiquitination and the like) or fragment thereof that is capable of binding to Integrin-bound fibronectin and undergoing internalization by tumor cells.

EMBODIMENTS

In accordance with one embodiment compositions and methods are provided to enhance the uptake of diagnostic and therapeutic agents by mammalian cells, including for example bladder cells, particularly bladder tumor cells of cancer patients. Uptake of materials by bladder cells is complicated due to the physical structure and environment of the bladder. Although fibronectin attachment protein (FAP) has been identified as the targeting molecule used by *Mycobacterium bovis* to bind to bladder tumor cells, most strategies using such a protein for selective uptake of bioactive agents have failed to provide adequate uptake of the complexes under serum-free, bladder lumen-like conditions.

Applicants have discovered that uptake of FAP by bladder tumor cells can be accelerated based on micro-aggregation of FAP. Accordingly, in one embodiment a method of enhancing the targeted uptake of therapeutic or diagnostic agents by a patient's cells is provided. The method comprises administering a complex of micro-aggregated FAP, wherein the complex is linked to a therapeutic or diagnostic agent to a patient. In accordance with one embodiment micro-aggregation of FAP is mediated by a carrier that comprises multiple ligands, in close proximity to one another (e.g., on a micron, submicron or nanoscale level), that bind to FAP.

In accordance with one embodiment the complex is administered for contact with bladder cells. The complex can be formulated in a pharmaceutically acceptable carrier and administered to the lumen of the bladder using standard techniques known to those skilled in the art. In one embodiment the pharmaceutical composition comprising the complex of micro-aggregated FAP is delivered by direct administration (via injection or by catheterization) of the composition into the bladder lumen. The pharmaceutical compositions can be further packaged as part of a kit that includes a disposable device for administering the composition to a patient. In one embodiment the kit is provided with a device for administering the composition to a patient. The kit may further include a variety of containers, e.g., vials, tubes, bottles, and the like. The kits will also include instructions for use.

In one embodiment the micro-aggregated FAP complex comprises a plurality of ligands that bind to FAP, wherein the ligands held within 100-150 nm of each another. In one embodiment the micro-aggregated FAP complex comprises a plurality of antibodies bound to FAP. In another embodiment the micro-aggregated FAP complex comprises a liposome bearing a plurality of ligands on the external surface of the liposome and the diagnostic agent or therapeutic agent is encapsulated within the liposome. The ligands on the external surface of the liposome may be antibodies that specifically bind to FAP or fusion peptides comprising a functional fibronectin attachment protein. Alternatively the ligands can be any moiety that binds to FAP or fusion peptides comprising a functional fibronectin attachment protein. In one embodiment the ligand is an entity capable of binding to peptide tag that has been added to a functional fibronectin attachment protein fusion peptide. For example a FAP fusion peptide can be produced with a His 6 (six histidine residues) and the corresponding ligand would be a Nickel bearing moiety (Ni2+NTA).

In accordance with one embodiment the micro-aggregation of FAP is mediated by either an anti-FAP polyclonal antibody or multivalent Ni2+NTA-bearing liposomes (or nanocarrier). In one embodiment FAP internalization can be induced by sequential incubation with a monoclonal antibody directed against FAP and then a second polyclonal antibody specific for the monoclonal antibody. According to one embodiment, enhanced uptake of FAP is used for FAP-mediated uptake of cytotoxic cargo-coupled antibodies and/or cytotoxic cargo-loaded liposomes.

In accordance with one embodiment a polyvalent complex is provided wherein the complex comprises a plurality of fibronectin attachment proteins covalently linked to one another. In one embodiment a plurality of FAP are covalently attached to one another through a linker. In one embodiment the linker is a peptide that links the individual FAP to one another. In one embodiment the peptides are linked to one another in a head to tail fashion. In another embodiment the linking moiety links the individual FAP to one another through the amino acid side chains of the proteins either directly through disulfide bonds of cysteine residues or alternatively through a peptide or non-peptide linker. In one embodiment the FAPs are linked to one another via a polyethylene linker.

In one embodiment a multivalent linking moiety is provided, wherein the multivalent linking moiety provides a scaffold for attaching a plurality of fibronectin attachment proteins either directly or through a linker. In one embodiment the multivalent linking moiety comprises a plurality of ligands that specifically bind to a fibronectin attachment proteins. In one embodiment the complex further comprises a diagnostic agent or a therapeutic agent linked to the multivalent linking moiety. The diagnostic agent can be linked either directly to the backbone of the multivalent linking moiety, or the agent can be linked indirectly through a linker, including encapsulation within a liposome or similar carrier, wherein the liposome/carrier is then tethered to the multivalent linking moiety.

In one embodiment the fibronectin attachment protein is linked to the multivalent linking moiety via a ligand. In one embodiment the ligand comprises an antibody that is specific for the fibronectin attachment protein, and in one embodiment the antibody is a monoclonal antibody. In an alternative embodiment, the fibronectin attachment protein is modified to further comprise a tag that is capable of interacting with a known ligand. For example the fibronectin attachment protein can be biotinylated or expressed as a fusion peptide further comprising a peptide tag. In one embodiment the fibronectin attachment protein is a fusion peptide comprising a peptide tag that is recognized by a monoclonal antibody. In one embodiment the multivalent linking moiety is an antibody-bearing liposome, wherein the antibodies are specific for the peptide tag of a fusion peptide comprising the fibronectin attachment protein and a peptide tag. In another embodiment the fibronectin attachment protein is expressed with a poly histidine tail and a metal chelator serves as the ligand. In one embodiment the multivalent linking moiety is $Ni^{2+}$NTA-bearing liposome.

In accordance with one embodiment a submicron polyvalent complex is provided for enhancing the uptake of a functional fibronectin attachment protein, and more particularly a functional fibronectin attachment protein that is linked to a diagnostic agent or a therapeutic agent (e.g., an anti-cancer or cytotoxic agent). The complex comprises a multivalent linking moiety, wherein said multivalent linking moiety comprises a plurality of ligands that specifically bind to a functional fibronectin attachment protein, and further includes a diagnostic or therapeutic agent linked to the polyvalent complex such that uptake of the functional fibronectin attachment protein also results in uptake of the diagnostic or therapeutic agent. In one embodiment the multivalent linking moiety is an antibody specific for the functional fibronectin attachment protein and the therapeutic agent is linked to the constant domain of the antibody, with the two antigen binding sites of the antibody representing the two "ligands" of the multivalent linking moiety. In one embodiment the antibody does not bind directly to the functional fibronectin attachment protein, but instead binds to a peptide tag that has been added to the functional fibronectin attachment protein sequence. In one embodiment the functional fibronectin attachment protein is a recombinant fusion peptide that comprises a non-native peptide tag. Accordingly, in one embodiment a polyvalent complex is provided comprising a multivalent linking moiety having a plurality of ligands that specifically bind to a functional fibronectin attachment protein, a diagnostic or therapeutic agent linked to the polyvalent complex, and a functional fibronectin attachment protein bound to said ligands, wherein the target functional fibronectin attachment protein is a recombinant fusion peptide comprising a peptide tag and the peptide tag specifically binds to the ligand.

In one embodiment the multivalent linking moiety is a liposome, wherein the plurality of ligands are presented on the external surface of the liposome and the diagnostic agent or therapeutic agent is encapsulated within the liposome. The plurality of ligands present on the exterior surface of the liposome can be antibodies specific for fibronectin attachment protein or for fusion peptides comprising a functional fibronectin attachment protein. Alternatively, the ligand can be any moiety capable of specific binding to fibronectin attachment protein or to fusion peptides comprising a functional fibronectin attachment protein. In one embodiment the ligands specifically bind to a non-native peptide tag present on a recombinant fusion peptide comprising the functional fibronectin attachment protein. In one embodiment, the fibronectin attachment protein is a recombinant fusion peptide comprising a histidine peptide tag and the multivalent linking moiety is $Ni^{2+}$NTA-bearing liposome.

Since within the bladder, fibronectin attachment protein specifically binds to ligands only exposed on bladder tumors, the complexes multivalent for fibronectin attachment proteins as disclosed herein can be used as an intelligent drug carrier capable of selective delivery of a drug (such as an anti-tumor agent). If a complex comprising multiply linked FAP is further linked with a conventional anti-tumor agent, it is possible to increase the efficacy of the anti-tumor agent and significantly reduce side effects adversely affecting normal tissue because the anti-tumor agent is delivered selectively to a bladder tumor cell by the multivalent complexes disclosed herein. In accordance with one embodiment the FAP/anti-tumor complexes can be further provided with additional cancer targeting moieties (e.g., anti-tumor antibodies) to further target the complexes to cancer cells.

In accordance with one embodiment a method of enhancing the targeted uptake of therapeutic or diagnostic agents by a patient's bladder tumor cells is provided. The method comprises the steps of providing a multivalent linking moiety, wherein the multivalent linking moiety comprises a linked therapeutic or diagnostic agent and a plurality of linked fibronectin attachment proteins (i.e., FAP, or a derivative or active fragment thereof), and administering said complex to the patient. In one embodiment the composition is delivered by direct administration (via injection or by catheterization) of the composition into the bladder lumen.

There is no particular limitation in the anti-tumor agent that may be linked with the peptide according to the present invention, and particular examples of such anti-tumor agents include docetaxel, mitoxanthrone, gemcitabine, capecitabine, oxaliplatin, interferon, sunitinib, sorafinib, cis- or carboplatinum, doxorubicin, methotrexate, vincristin, vinorelbine, pemetrexed, gefitinib, etoposid, irinotecan, cyclophosphamide, topotecan, cyclophosphamide, paclitaxel, mitomycin, bevacizumab, trastuzumab, 5-fluorouracil, cetuximab, temozolomide, bevacizumab, procarbacine, cisplatin, adriamycin, vinblastine, busulfan, chlorambucil, cyclophosphamide, melphalan, CCNU, and BCNU. Preferably, the complex can be linked to an anti-tumor agent effective for the treatment of a bladder tumor. Linking of the anti-tumor agent with the complex can be performed by using a conventional method generally known to one skilled in the art, including covalent bonding, crosslinking, etc.

In addition, the composition according to the present invention may further comprise pharmaceutically acceptable carriers that are added conventionally to a general pharmaceutical composition. In the case of injection formulation, particular examples of the pharmaceutically acceptable carriers include a buffering agent, a preserving agent, an anesthetic agent, a solubilizing agent, an isotonic agent and a stabilizer. The composition can as a unit dose ample or a multidose vial.

A "liposome" as used herein refers to a small, spherical vesicle composed of lipids, particularly vesicle-forming lipids capable of spontaneously arranging into lipid bilayer structures in water with its hydrophobic moiety in contact with the interior, hydrophobic region of the bilayer membrane, and its head group moiety oriented toward the exterior, polar surface of the membrane. Vesicle-forming lipids have typically two hydrocarbon chains, particularly acyl chains, and a head group, either polar or nonpolar. Vesicle-forming lipids are either composed of naturally-occurring lipids or of synthetic origin, including the phospho lipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospho lipids whose acyl chains have varying degrees of saturation can be obtained commercially or prepared according to published methods. Other suitable lipids for use in the composition of the present invention include glycolipids and sterols such as cholesterol and its various analogs which can also be used in the liposomes.

Cationic lipids, which typically have a lipophilic moiety, such as a sterol, an acyl or diacyl chain, and where the lipid has an overall net positive charge can also be suitably used in liposomes. The head group of the lipid typically carries the positive charge. Exemplary cationic lipids include 1,2-dioleyloxy-3-(trimethylamino)propane (DOTAP); N-[1-(2,3,-ditetradecyloxy)propyl]-N,N-dimethyl-N-hydroxyethyl-ammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethyl-ammonium chloride (DOTMA); 3[N—(N',N'-dimethylaminoethane)carbamoyl]cholesterol(DC-Chol); and dimethyl-dioctadecylammonium (DDAB). The cationic vesicle-forming lipid may also be a neutral lipid, such as dioleoylphosphatidyl ethanolamine (DOPE) or an amphipathic lipid, such as a phospho lipid, derivatized with a cationic lipid, such as polylysine or other polyamine lipids.

The liposomes can include a vesicle-forming lipid derivatized with a hydrophilic polymer to form a surface coating of hydrophilic polymer chains on the liposomes surface. A vesicle-forming lipid, in particular a phospho lipid, such as distearoyl phosphatidylethanolamine (DSPE), may be covalently attached to a hydrophilic polymer, which forms a surface coating of hydrophilic polymer chains around the liposome. Hydrophilic polymers suitable for derivatization with a vesicle-forming lipid include polyvinylpyrrolidone, polyvinylmethylether, polymethyloxazo line, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences. The polymers may be employed as homopolymers or as block or random copolymers.

One hydrophilic polymer chain suitable for use is polyethyleneglycol (PEG), preferably as a PEG chain having a molecular weight between 200-20,000 daltons, or between 500-10,000 daltons, or between 750-5000 daltons. Methoxy or ethoxy-capped analogues of PEG are also preferred hydrophilic polymers, commercially available in a variety of polymer sizes, e.g., 120-20,000 Daltons. In one embodiment the PEG polymers are derivatized (e.g. at the free end) to further comprise a ligand that binds to a fibronectin attachment protein.

Preparation of Vesicle-Forming Lipids Derivatized with Hydrophilic Polymers has been described, for example in U.S. Pat. No. 5,395,619, in U.S. Pat. No. 5,013,556, in U.S. Pat. No. 5,631,018 and in WO 98/07409. It will be appreciated that the hydrophilic polymer may be stably coupled to the lipid, or coupled through an unstable linkage, which allows the coated liposomes to shed the coating of polymer chains as they circulate in the bloodstream or in response to a stimulus. In one embodiment the liposomes are derivatized to include a plurality of antibodies or ligands that specifically bind to a fibronectin attachment protein.

Example 1

Investigation of the Mechanism and Kinetics of FAP Uptake by Bladder Tumor Cells In a serum-free environment such as the lumen of the bladder, internalization of FAP-fibronectin (FBN)-Integrin complexes occurred with a very slow kinetics. This internalization process can be greatly accelerated by micro-aggregation of FAP-FBN-integrin complexes. As disclosed in the following experiments, purified FAP is internalized by a clathrin-independent mechanism, routed to the lysosome in T24 bladder tumor cells. Accordingly, based on these results, FAP can be used in promoting nano-liposome internalization and provide the means for designing FAP-targeted carriers for the efficient delivery of cytotoxic agents.

Materials and Methods

Materials

Dulbecco's Modification of Eagle's Medium (DMEM) with 4.5 g/L glucose and sodium pyruvate without L-glutamine was purchased from Cellgro (Manassas, Va.). 1,2-Dipalmitoyl-sn-glycero-3-phosphocholine (DPPC) and 1,2-distearoyl-sn-glycero-3-phosphoethanolamine (DSPE) was purchased from Avanti Polar Lipids (Alabaster, Ala.) as a chloroform stock solution and lyophilized powder, respectively. CFTM-633 succinimidyl ester was purchased from Biotium, Inc. (Hayward, Calif.). All other compounds were purchased from Aldrich and used without further purification unless otherwise stated.

1,3-Disteareylglycerol-PEG2000-NTA (DSG-PEG2K-NTA)

This compound was synthesized as described in Hyun, et al., *Bioconjug. Chem.*, 2006, 17, 1592-1600.

DSPE-CF™-633

DSPE was dissolved in dry DCM and then transferred to 1 mL vial with CF™-633 succinimidyl ester. The mixture was placed on a shaker and mixed overnight before passing it through a lipophilic Sephadex LH-20 column that had been equilibrated with 10% MeOH in DCM. Column fractions were evaporated to dryness and then redissolved in 1 mL of chloroform for use in liposome formulations.

$Ni^{2+}$:trisNTA-AlexaFluor 647

Full description of the synthesis of this reagent can be found in the Supplemental Material section. Briefly, Boc-protected $N^{\alpha}$-tris(nitrilotriacetic acid)-$N^{\epsilon}$-benzoyl-lysine was prepared as described by Szoka and coworkers (see Huang, et al, *Bioconjugate Chem.* 2006, 17, 1592-1600). Hydrogenolysis of the benzoyl group from this intermediate followed by condensation with AlexaFluor 647 N-hydroxysuccinimidyl ester and global deprotection with trifluoroacetic acid in dichloromethane gave the metal-free trisNTA-AlexaFluor 647 species. Treatment of this species with stoichiometric quantities of $NiSO_4$ in water gave the nickel-activated reagent, $Ni^{2+}$:trisNTA-AlexaFluor 647, as a stock solution that was used for labeling $His_6$-FAP for subsequent cellular localization studies.

Cell Lines, Culture Conditions and Reagents.

T24 bladder carcinoma cells were cultured in DMEM, streptomycin/penicillin, 2 mM L-glutamine and 10% fetal bovine serum. Normal human dermal fibroblasts were obtained from the Coriell cell repository and cultured as previously described (Coon et al. Hum Mol Genet 2009; 18: 4478-91). Transfections of plasmid DNA and siRNAs were performed using FugeneHD (Roche) and TransIT-TKO (Minis) reagents, respectively, according to manufacturer's instructions. Plasmid transfections were conducted 18-30 h before use. siRNA transfections were performed twice at 72 and 48 h before use.

Protein Purification.

Bacterially produced recombinant proteins were generated in Rosetta cells (Novagen) by inducing expression of pTrc-his plasmids with 0.05 mM IPTG for 5 h at 30° C. Proteins were purified in PBS, 0.1% Tween, and 15% glycerol using $Ni^{2+}$NTA resin (Novagen) according to standard protocols and eluted with PBS, 250 mM imidazole for 2-8 h at 4° C. The eluate was then desalted with Pierce Zeba Spin columns into PBS. The purified FAP concentration was measured using Precision Red protein assay reagent (Cytoskeleton) before dilution to a final concentration of 10 µM in DMEM or an otherwise indicated buffer. Bladder instillation buffer (Buffer 9B) was composed of 30 mM NaCl, 15 mM $Na_2HPO_4$, 90 mM $KH_2PO_4$, 0.6 mM $MgSO_4$, 2.5 mM Citrate pH=7.2.

FAP Binding.

Cells were seeded on coverslips for approximately 24 h before use to allow secretion and organization of extracellular fibronectin structures. FAP 10 µM in the indicated buffers was added and incubated with cells for 3 h at 37° C. to enable optimal cell binding. Cells were then fixed in 3% formaldehyde for 10 min and processed for immunofluorescence and microscopy as previously described (Coon et al. Hum Mol Genet 2009; 18: 4478-91).

Internalization Experiments—

For FAP internalization assays, T24 cells were seeded on poly-L-lysine-coated coverslips for 8-24 h before initiation of endocytosis experiments via starvation in DMEM+0.1% FBS for 4 h. FAP (10 µM in DMEM), was then added to the cells and incubated for 1 h at 37° C. to allow binding to the cell surface. Then, in order to label surface protein and induce clustering, cells were rinsed with PBS and immersed in DMEM with 25 µM $Ni^{2+}$:trisNTA-AlexaFluor647 and indicated antibodies for 45 min at 10° C. Cells were rinsed with PBS, transferred to a 37° C. incubator for the indicated times to allow internalization, and then fixed in 3% formaldehyde for 10 min. In the absence of $Rab5^{Q79L}$, lysosomal degradation was prevented by incubating cells with 100 µg/mL leupeptin.

To quantify FAP internalization, 3-slice z-stack images were acquired with a Zeiss Axiovert 200M microscope equipped with an Axiocam MRm camera and standard Zeiss filter cubes including filter set 50 (ex: BP640/30, bs: FT660, em: BP690/50) for AlexaFluor647 and CF633 imaging. Stacks were transferred to ImageJ and the images processed as described (Coon et al. Hum Mol Genet 2009; 18: 4478-91). The signal intensity of $Ni^{2+}$:trisNTA-AlexFluor647-labeled FAP was then measured within either the $Rab5^{Q79L}$-GFP structures or in whole cells using a freehand ROI and substracted from background intensity. The resultant intensity units were then multiplied by the ROI area to obtain arbitrary fluorescence units for each cell. Transferrin-AlexaFluor488 internalization experiments were performed as previously described (Coon et al. *Hum Mol Genet* 2009; 18: 4478-91).

Liposome Preparation

Liposomes were prepared by the thin film hydration method. A chloroform solution of DPPC:Chol:DSG-PEG2K-NTA:DSPE-CF™-633 mixed at a 64:35:0.5:0.5 molar ratio (13 µmol total lipid) was carefully evaporated under a flow of $N_2$ gas, producing an even, thin film. The film was placed under a 50 µm Hg vacuum for 3 h to remove trace solvent impurities. This film was then hydrated in 4 mL DMEM 1× media solution via 10 freeze-thaw-vortex cycles. The resulting multilamellar liposome solution was then extruded seven times at 50-55° C. through three stacked polycarbonate filters of 800 nm, 200 nm and 50 nm pore diameter using an Extruder device that was charged with 200-300 psi $N_2$ pressure.

Recycling Experiments

A) Direct Measurement of Recycling:

This experimental approach is designed to measure a putative decrease in the pool of internalized $His_6$-FAP as a function of time due to recycling.

T24 cells were treated with leupeptin and bound to $His_6$-FAP as described in above. Then $His_6$-FAP was fluorescently labeled with 25 µM $Ni^{2+}$:trisNTA-AlexaFluor-647 and clustered with 1/1000 anti-FAP antibodies as described for the endocytosis experiments. After 3 h of internalization at 37° C. in the presence of serum-free DMEM and 100 µg/mL leupeptin, non-internalized surface probes (both $Ni^{2+}$:trisNTA-AlexaFluor647 and anti-FAP) were removed by rinsing cells with pH 2.0 buffer supplemented with 20 mM EDTA for 60 s. After washing, cells were allowed to recycle internalized $His_6$-FAP for up to 1.5 h before removing putative recycled FAP and fixing. Internalized FAP and the lysosomal marker Lamp2 were investigated by immuno fluorescence with specific antibodies.

B) Inhibition of Recycling.

This approach aims to detect accumulation of internalized FAP upon inhibition of recycling and lysosomal degradation. In T24 cells treated with 100 μg/mL leupeptin, recycling was impaired by overexpressing constitutively inactive Rab4 and Rab11 constructs.

Organic Synthesis Methods

Figure 7:
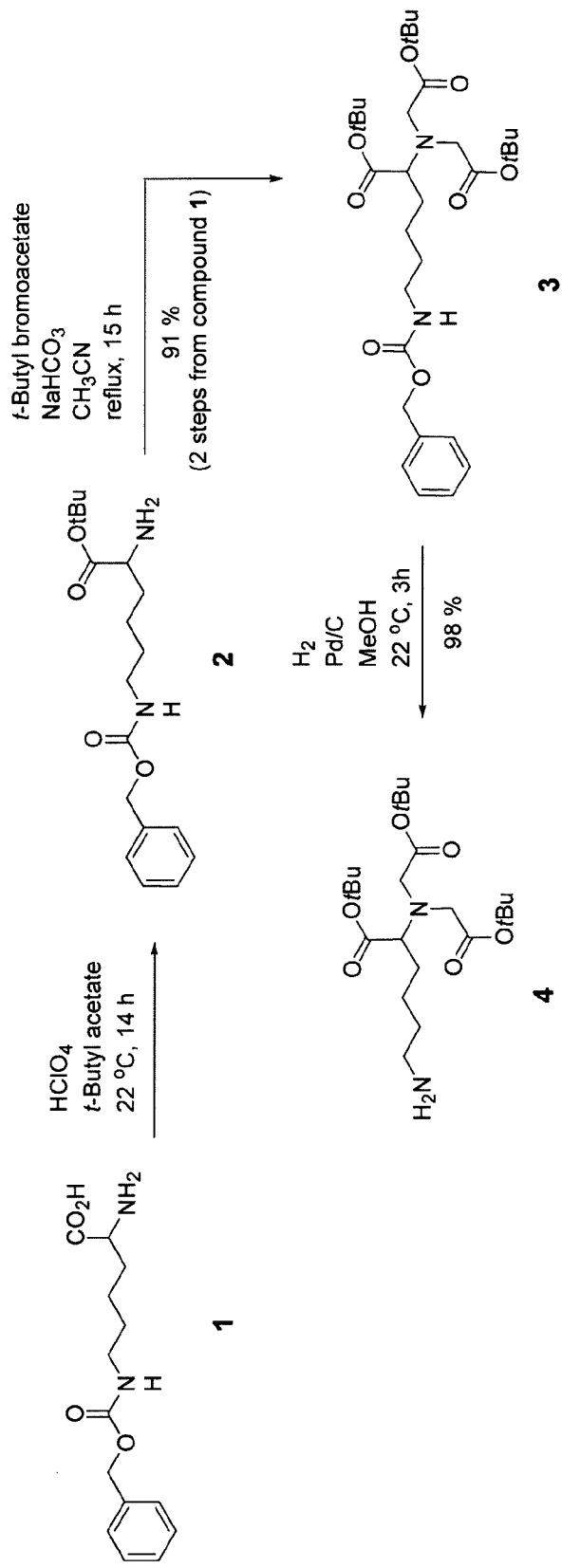
FIG. 7 is a schematic drawing of the synthesis route for the preparation of lysine NTA intermediate. See Example 1 for details.
Figure 8:
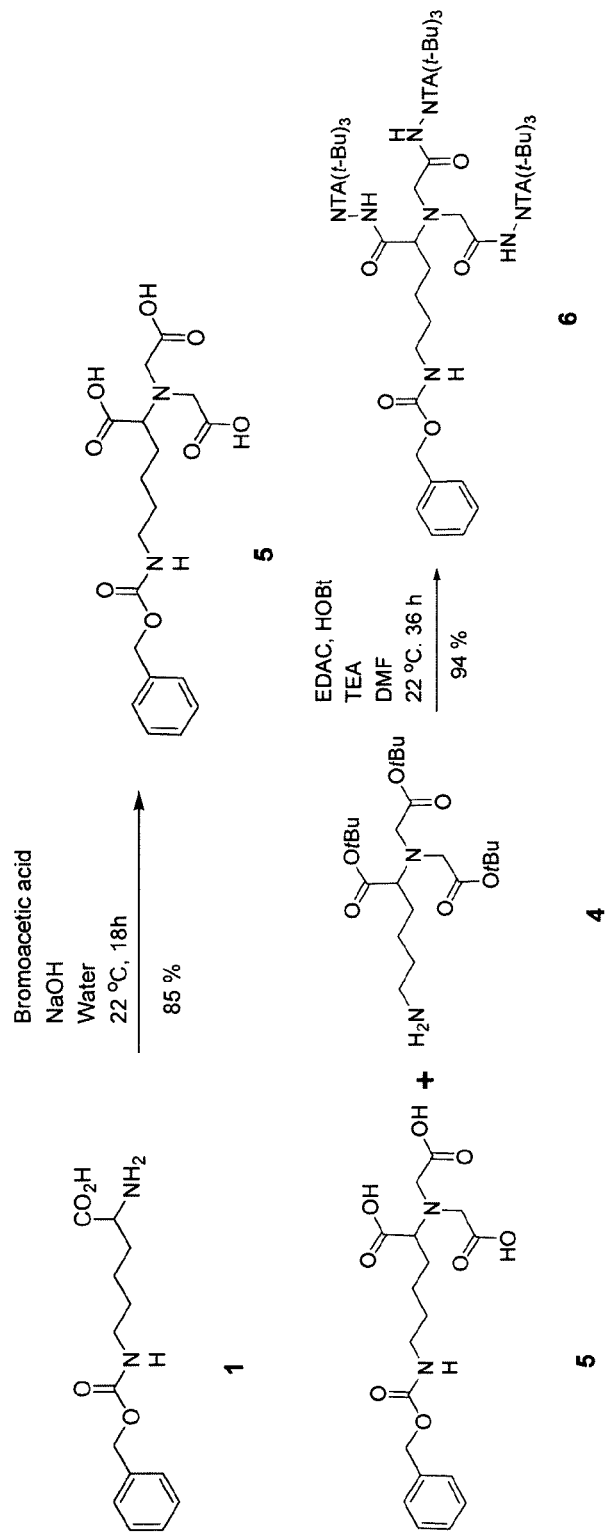
FIG. 8 is a schematic drawing of the TrisNTA-AlexaFluor 647 synthesis pathway. See Example 1 for details.
Figure 8:
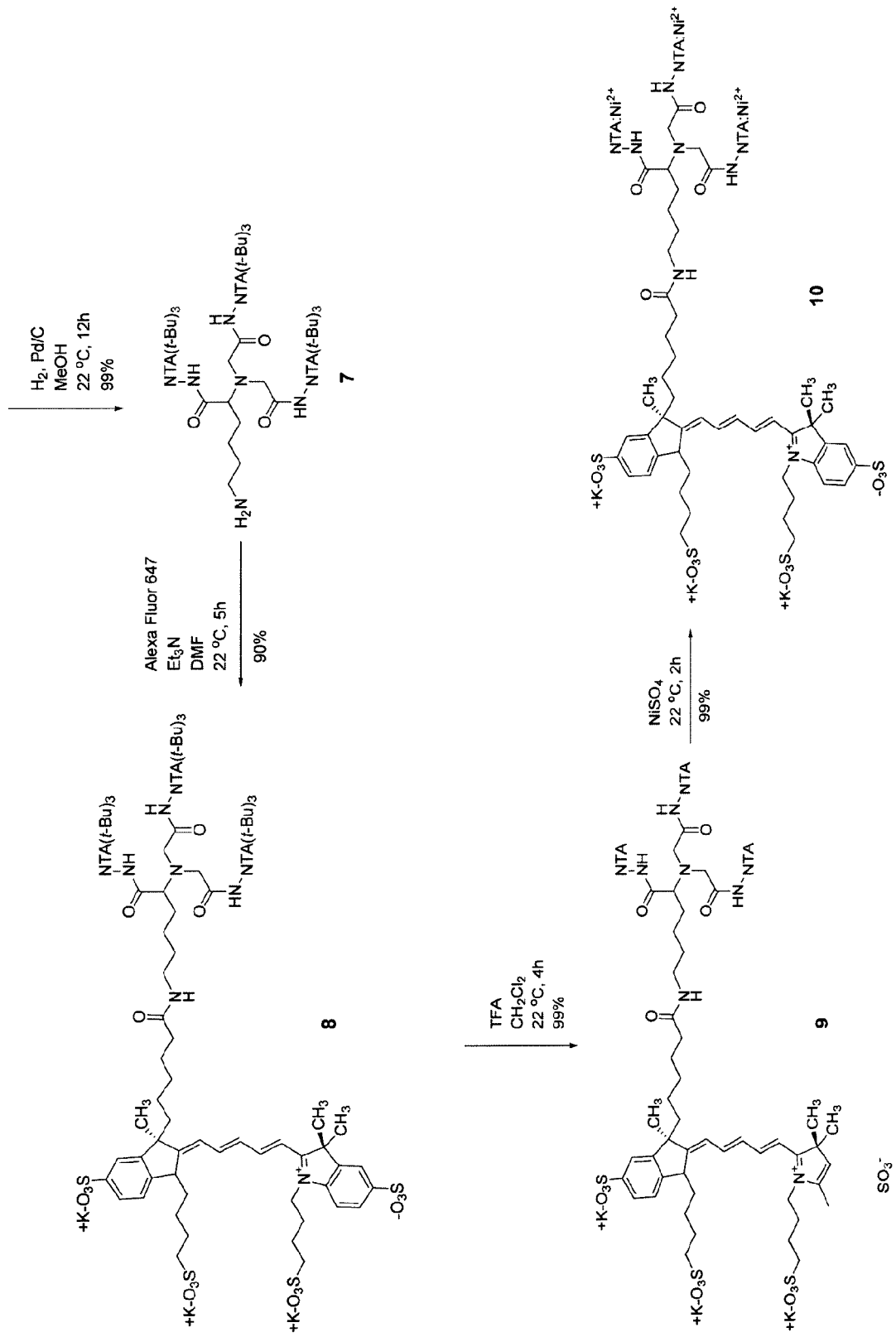
Figure 8:
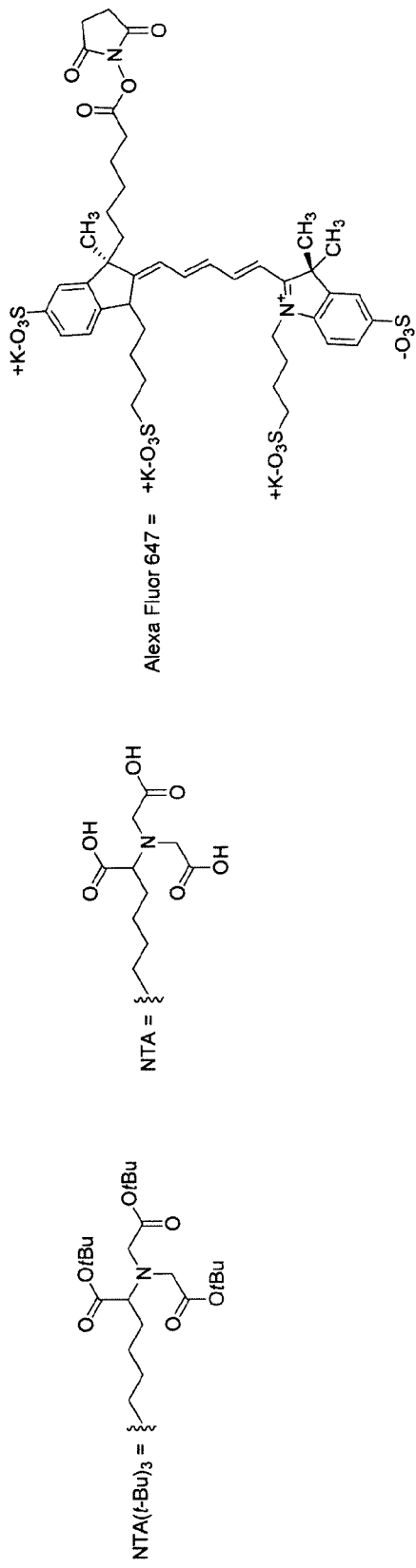

All reagents were obtained from commercial suppliers and used without further purification unless otherwise noted. All reactions (FIGS. 7 and 8) were carried out under a blanket of $N_2$ gas. Reaction progress was monitored by thin-layer chromatography (TLC) analysis. TLC spots were visualized by UV light (254 nm) exposure. $CH_3CN$ was distilled from $CaH_2$. Flash column chromatography was carried out using 230-400 mesh silica gel and analytical grade solvents. $^1H$ and $^{13}C$ nuclear magnetic resonance (NMR) spectra were recorded with a Varian INOVA (300 MHz) spectrometer. Chemical shifts are reported in ppm relative to the residual solvent peaks as internal standard. Peak multiplicities in $^1H$ NMR spectra are abbreviated as s (singlet), d (doublet), t (triplet), dd (doublet of doublet), m (multiplet), and br (broad). Mass spectrometry was performed by the MCMP Mass Spectrometry Service of Purdue University.

Di-t-butyl 2,2'-((6-(((benzyloxy)carbonyl)amino)-1-(t-butoxy)-1-oxohexan-2-yl)azanediyl)diacetate (3)

$HClO_4$ (3.01 mL) was slowly added to a stirred solution of Z-Lys 1 (6.5 g, 23.18 mmol) in t-butyl acetate (80 mL). The mixture was stirred at 22° C. for 14 h before extracting with $H_2O$ (150 mL) and 0.5N HCl solution (150 mL). The combined aqueous solutions were treated with 10% $K_2CO_3$ to give a solution of pH 9; the basic solution was then extracted with $CH_2Cl_2$ (3×100 mL). The combined organic layers were dried over anhydrous $MgSO_4$, filtered, and then concentrated to give 2 as a colorless oil. The oil was dissolved in $CH_3CN$ (150 mL) before addition of $NaHCO_3$ (4.29 g, 51.07 mmol) and t-butyl bromoacetate (13.58 g, 69.64 mmol). The mixture was heated at reflux for 15 h, then cooled to 22° C. before concentration of the mixture under reduced pressure and extraction of the residue with ethyl acetate (2×150 mL). The combined organic layers were washed with saturated NaCl solution (2×100 mL), dried over anhydrous $MgSO_4$, and evaporated. The crude residue was purified by silica gel flash chromatography using 4:1 hexane:EtOAc as eluent to give compound 3 (11.62 g, 91%) as a colorless oil. 1H NMR (300 MHz, CDCl3) δ 7.30-7.35 (m, 5H), 5.08 (s, 2H), 3.44 (dd, J=17.4, 11.1 Hz, 4H), 3.30 (t, J=7.35 Hz, 1H), 3.20 (m, 2H), 1.62 (m, 2H), 1.53 (m, 4H), 1.45 (s, 9H), 1.43 (s, 18H); 13C NMR (75 MHz, CDCl3) δ 172.2, 171.2, 157.0, 137.34, 128.9, 128.6, 128.4, 81.64, 81.2, 66.9, 65.6, 54.4, 41.3, 30.6, 29.8, 28.7, 28.6, 23.5; HRMS (ESI): (M+H)+ m/z calc'd for C30H48N2O8=564.7107. found 565.0643. The NMR spectra are in agreement with previously published data. (Huang et al Bioconjugate Chem. 2006, 17, 1592-1600).

Di-t-butyl 2,2'-((6-amino-1-(t-butoxy)-1-oxohexan-2-yl)azanediyl)diacetate (4)

Compound 4 was synthesized according to a previously published procedure (Hussein et al. J. Org. Chem. 2009, 74, 1473-1479).

2,2'-((5-(((Benzyloxy)carbonyl)amino)-1-carboxypentyl)azanediyl)diacetic acid (5)

Compound 5 was synthesized according to a previously published procedure (Altin et al. Aust. J. Chem. 2006, 59, 302-306).

Tetra-t-butyl 10-(4-(((benzyloxy)carbonyl)amino) butyl)-11-(2-((5-(bis(2-(t-butoxy)-2-oxoethyl) amino)-6-(t-butoxy)-6-oxohexyl)amino)-2-oxo-ethyl)-2,20-bis(2-(t-butoxy)-2-oxoethyl)-9,13-dioxo-2,8,11,14,20-pentaazahenicosane-1,3,19,21-tetracarboxylate (6)

EDC (83 mg, 430 μmol) and HOBt (48 mg, 357 μmol) were added to a solution of 5 (40 mg, 110 μmol) in anhydrous DMF (8 mL) at 0° C. After stirring the mixture for 15 min at 0° C., a solution of 4 (148 mg, 487 μmol) and triethylamine (151 μL, 1.1 mmol) was added at 0° C. After stirring the reaction at 22° C. for 24 h, the mixture was concentrated under reduced pressure and extracted with CH2Cl2 (2×15 mL). The crude residue was purified by silica gel flash chromatography using 10:1 CH2Cl2:MeOH as eluent to give 7 (167 mg, 94%) as an oil. 1H NMR (300 MHz, CDCl3) δ 7.34 (m, 5H), 5.08 (s, 2H), 3.45 (m, 16H), 3.19-3.31 (m, 12H), 1.65 (m, 8H), 1.53 (m, 16H), 1.46 (s, 27H), 1.44 (s, 54H); 13C NMR (75 MHz, CDCl3) δ 172.3, 171.5, 170.7, 162.6, 156.5, 136.8, 128.5, 127.981.1, 80.7, 66.4, 65.0, 56.2, 53.7, 40.6, 39.3, 31.4, 30.2, 29.9, 29.5, 29.3, 28.7, 28.2, 28.1, 23.4, 23.1; MS (positive ESI): (M+H)+m/z calc'd for C84H144N8O23=1633.03. found 1633.90. The NMR spectra are in agreement with previously published data.

Tetra-t-butyl 10-(4-aminobutyl)-11-(2-((5-(bis(2-(t-butoxy)-2-oxoethyl)amino)-6-(t-butoxy)-6-oxo-hexyl)amino)-2-oxoethyl)-2,20-bis(2-(t-butoxy)-2-oxoethyl)-9,13-dioxo-2,8,11,14,20-pentaazahenicosane-1,3,19,21-tetracarboxylate (7)

Palladium on carbon (500 mg of 10 wt % Pd/C) was added to a solution of 6 (1.6 g, 979 μmol) in MeOH (30 mL). After stirring the reaction at 22° C. for 12 h under 1 atm H2, the mixture was filtered and evaporated under reduced pressure to give 7 (1.5 g, 99%). 1H NMR (300 MHz, CDCl3) δ 3.42 (m, 16H), 3.21-3.29 (m, 12H), 1.79 (m, 4H), 1.52 (m, 16H), 1.41 (s, 27H), 1.40 (s, 54H); 13C NMR (75 MHz, CDCl3) δ 172.4, 170.8, 81.2, 81.1, 65.2, 53.8, 39.2, 30.3, 29.0, 28.2, 28.1, 23.5, 23.3; MS (positive ESI): (M+H)+ m/z calc'd for C76H138N8O21=1499.00. found 1499.95. The NMR spectra are in agreement with previously published data (Huang et al Bioconjugate Chem. 2006, 17, 1592-1600).

Compound 8. Compound 7 (1.5 mg, 1 mmol) was added to a solution of Alexa Fluor 647 maleimide (1 mg, 800 μmol) and triethylamine (11 μL, 8 mmol) in DMF (5 mL). After stirring the reaction at 22° C. for 5 h, the mixture was passed through a Sephadex G-15 column and the eluate lyophilized to give 8 (2 mg, 90%).

trisNTA-AlexaFluor 647 (9)

Compound 8 (2 mg, 727 μmol) was diluted in dichloromethane (1 mL) and trifluoroacetic acid (0.7 mL). The reaction mixture was stirred at 22° C. for 4 h before concentrating the solution under reduced pressure to give 9 (1.6 mg, 99%).

Ni2+:trisNTA-AlexaFluor 647 (10)

NiSO4 (100 μL of 50 mM stock solution, 2.139 mol) was added to Compound 9 (1.6 mg, 713 μmol) in H2O (1.5 mL). The reaction mixture was stirred at 22° C. for 2 h before passing it through a Sephadex G-15 column, and lyophilization to give 10 (1.6 mg, 99%). A 25 μM stock solution of 10 was prepared for labeling $His_6$-FAP in subsequent cellular localization studies.

DSPE-CF™-633

DSPE was dissolved in dry $CH_2Cl_2$ and then transferred to 1 mL vial with CF1998-633 succinimidyl ester. The mixture was placed on a shaker and mixed overnight before passing it through a lipophilic Sephadex LH-20 column that had been equilibrated with 10% MeOH in $CH_2Cl_2$. Column fractions were evaporated to dryness and then re-dissolved in 1 mL of $CHCl_3$ for use in liposome formulations.

Results

Fibronectin Attachment Protein (FAP) Targets Fibronectin (FBN) and Integrins in Human Fibroblasts and Bladder Tumor Cells.

It has been demonstrated that BCG association with bladder cells is mediated by bacterial FAP. Further, it was also shown that binding of radio-iodinated FAP to FBN required the RWFV sequence (residues 213-216). In order to establish the mechanisms involved in the interaction of FAP with bladder tumor cells, the ability of recombinant purified FAP to specifically target cell-bound FBN structures was first determined by fluorescence microscopy analysis. We determined that purified FAP wt, but not $FAP^{\Delta 213-216}$, was able to bind cell-associated FBN. Specifically, Human dermal fibroblasts or T24 bladder cells grown on coverslips for 24 h were incubated with 10 μM $His_6$-FAP, washed, fixed and immunostained with anti-$His_6$ and either anti-FBN or anti-integrin antibodies. Human dermal fibroblasts, known to produce robust FBN networks, show a significant co-localization between purified $His_6$-FAP and both FBN and β1-Integrins. Although, less differentiated T24 bladder tumor cells showed less intricate FBN fibrilar networks, FAP was also co-localized with FBN on these cells.

Figure 6:
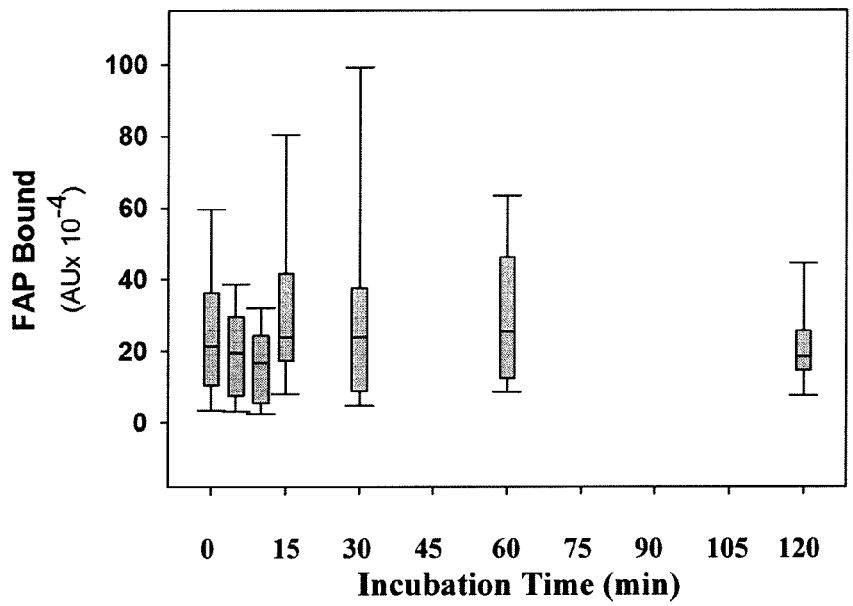
FIG. 6 The association of purified FAP with cell-bound Fibronectin is resistant to acidic and bladder instillation conditions. FAP binding to cell-associated Fibronectin was performed using the antibody-induced FAP micro-aggregation strategy. Following incubation with a pH=4.8 buffer (0.2N Acetic Acid, 150 mM NaCl) at room temperature for the indicated times, cells were fixed and immunostained with anti-His primary and anti-mouse AlexaFluor546 secondary antibodies. FAP fluorescence that remained associated with cells was quantified as described in Example 1 (AU: Arbitrary Units).

The capacity of the FAP-FBN complex to form under conditions that resemble the characteristics of the bladder lumen was next investigated. Specifically, we determined that FAP interaction with FBN was resistant to acidic treatment (pH=4.8 for several hours (FIG. 6). Furthermore, purified FAP was able to bind cell-associated FBN in the presence of a bladder instillation buffer ("Buffer 9B") capable of controlling pH even after a 1:2 dilution with urine. In addition, FAP could be observed in association with cell-bound FBN by using $Ni^{2+}$:trisNTA-AlexaFluor647 probe to target the $His_6$-tag present in the recombinant purified protein.

FAP's Low Internalization Rate by Bladder Tumor Cells can be Enhanced by Antibody-Induced Micro-Aggregation.

Therapeutic approaches based on the targeting of tumor cells are expected to be enhanced upon toxic cargo delivery by endocytosis. Therefore, we studied whether purified FAP could be internalized by bladder tumor cells.

Since FAP interaction with cellular FBN is resistant to low pH treatment (FIG. 6), standard endocytosis assays relying on acid washes to strip non-internalized ligand could not be used. Therefore, we relied on a different methodological approach based on the expression of a $Rab5^{Q79L}$-GFP constitutively activated mutant (locked in its GTP-bound conformation) for the detection of endocytosed FAP. Expression of this construct does not affect ligand-internalization rates, but leads to the formation of an easy to visualize, GFP-positive, enlarged endosomal compartment due to enhanced early endosome fusion (FIG. 1B and McGraw T E, Subtil A. Endocytosis: biochemical analyses. Curr Protoc Cell Biol 2001; Chapter 15: Unit 15 3). Consequently, we were able to readily identify internalized FAP based on its inclusion within enlarged $Rab5^{Q79L}$-GFP-decorated structures. Further, this Rab5 mutant also promotes the accumulation of internalized cargo in the $Rab5^{Q79L}$-containing endosomal compartment by interfering with lysosomal targeting. Therefore, expression of $Rab5^{Q79L}$-GFP led to an increased FAP-associated fluorescent signal as a function of time, thus enhancing the analytical sensitivity of our assays (see FIG. 1B). Unless indicated otherwise, we used this approach throughout this study.

Although we observed robust internalization of purified FAP under normal cell culture conditions, in the absence of serum (to emulate bladder lumen conditions), the kinetic of endocytosis was dramatically reduced. In fact, virtually no internalization was observed over incubation periods of several hours.

Figure 1B:

Therefore, we devised an approach to trigger FAP endocytosis upon antibody-induced, micro-aggregation of FAP-FBN-Integrin complexes at the plasma membrane (FIG. 1A). Specifically, following FAP binding (1 h at 37° C., determined to be optimal for FAP association with FBN without major incorporation into highly stable FBN fibrils) the cells were chilled, washed and labeled with a fluorescently-tagged $Ni^{2+}$:trisNTA probe. Either an anti-FAP polyclonal antibody (i.e., capable of crosslinking multiple FAP-FBN-Integrin complexes) or an irrelevant poyclonal antibody were also added to the cells and incubated for 45 min at 10° C. Then, the cells were washed and DMEM at 37° C. was added to promote clustering and internalization.

Figure 2A:
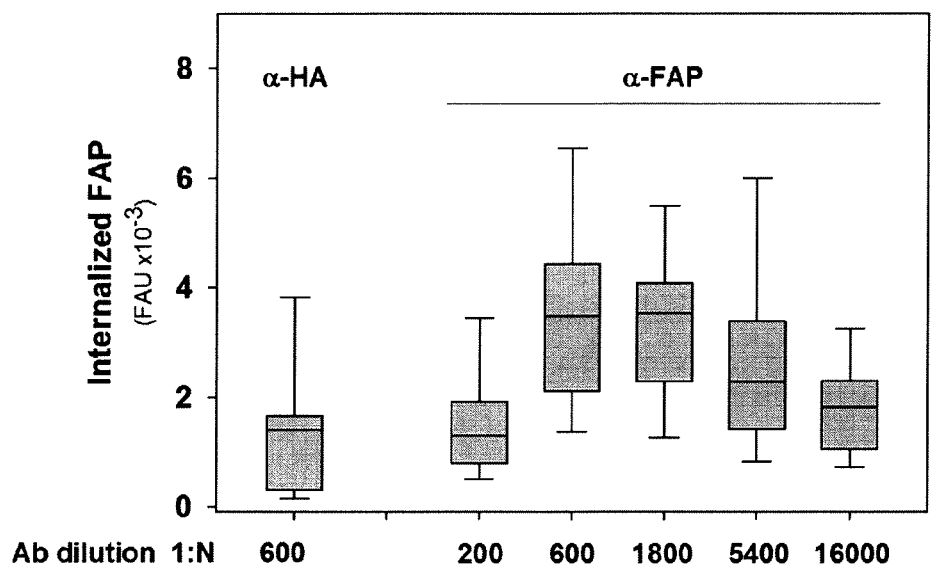
FIG. 2A-2B Antibody-dose dependence and kinetics of Antibody-induced FAP internalization.

Using this approach, we observed a significant uptake of FAP that was dependent on the antibody specificity. As further confirmation of this effect, an anti-$His_6$ monoclonal antibody also induced FAP uptake when crosslinked by a polyclonal secondary antibody. As expected, the internalization of FAP as a function of antibody concentration displayed a bell-shaped relationship (FIG. 2A). Specifically, we found that increasing the antibody dose was correlated with increased amounts of crosslinked FAP up to a maximum concentration; above this optimal concentration, saturation of the antigen with antibody occurred, such that the increasing extent of 1:1 antigen:antibody complexes led to decreased crosslinking and reduced levels of FAP internalization (FIG. 2A). These studies revealed a maximal amount of internalized FAP at 1:600-1:1800 dilutions (FIG. 2A); thus, a 1:1000 antibody dose was used in all subsequent experiments.

Figure 2B:
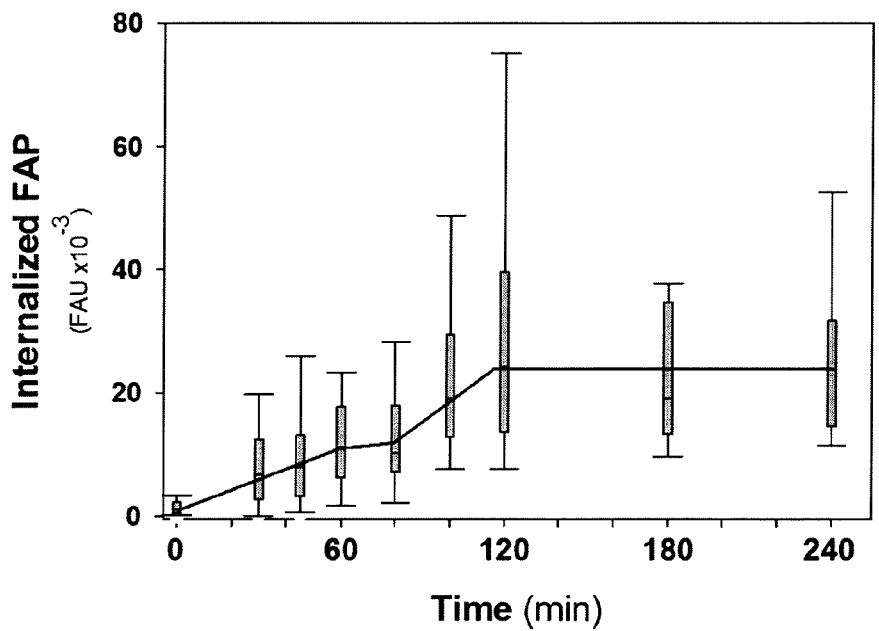

Next, we established the kinetics of antibody-induced FAP uptake (FIG. 2B). Our results indicate that internalized FAP started to accumulate in the $Rab5^{Q79L}$-GFP positive compartment immediately following chase and reached a plateau after approximately 2 h incubation (FIG. 2B). To ensure optimal FAP detection, unless indicated otherwise, we adopted a 3 h-incubation scheme in our following experiments.

FAP is Internalized by Clathrin-Independent, Caveolin-Dependent Endocytosis.

Figure 3A:
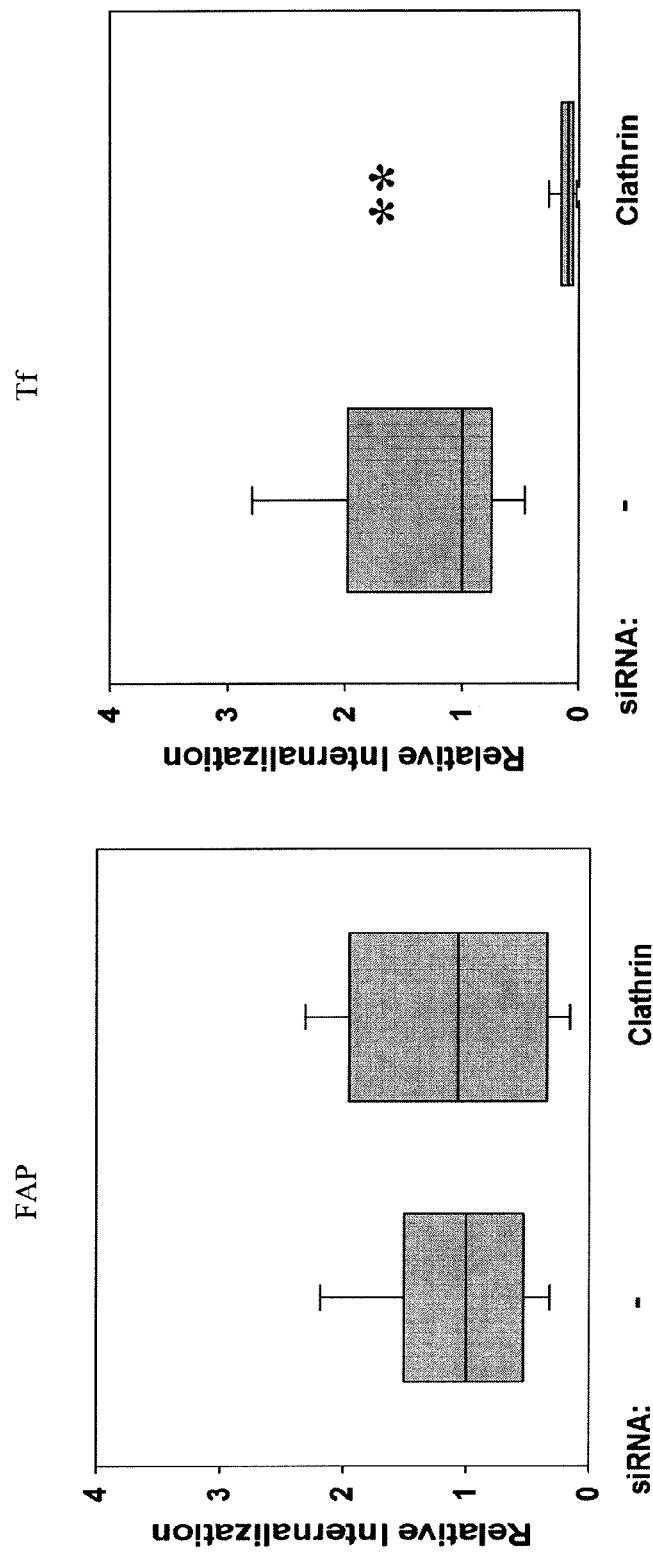
FIG. 3A-3C FAP is internalized by a clathrin-independent, caveolae-dependent mechanism.
Figure 3B:
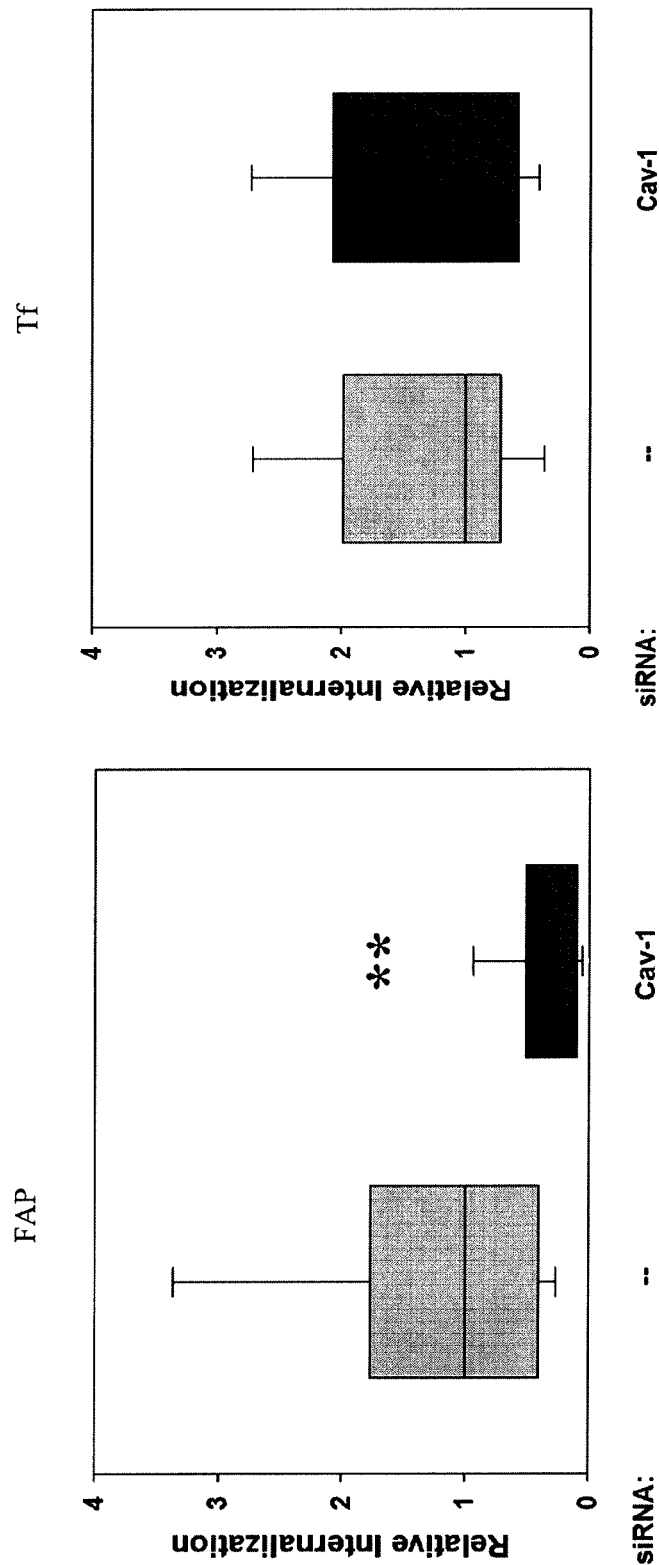
Figure 3C:
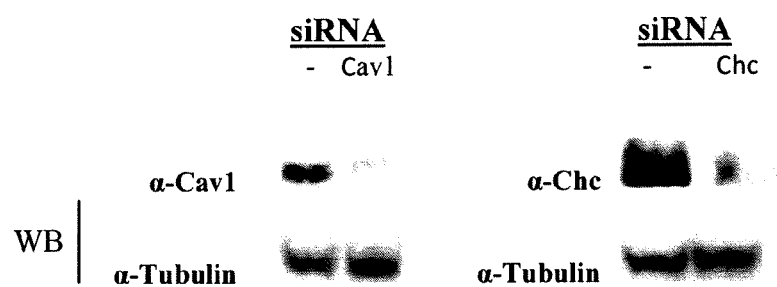

We hypothesize that the FAP-FBN-Integrin complex is internalized by a mechanism similar to that described for integrin uptake. However, both clathrin-dependent and clathrin-independent mechanisms have been proposed for internalization of integrin complexes. Therefore, we first determined whether FAP uptake was dependent or independent of clathrin. Our results indicate that siRNA-mediated knock-down of clathrin did not affect FAP uptake, but efficiently inhibited transferrin (Tf)s internalization (FIG. 3A). Further, no significant co-localization was observed between cell-bound FAP and clathrin-coated areas. In contrast, FAP showed strong colocalization with caveolae and its uptake was inhibited by siRNA-mediated knock-down of Caveolin-1(Cav-1; see FIG. 3B). The efficiency of the siRNA-mediated knock-down was revealed by Western blotting with specific antibodies (FIG. 3C).

FAP is Targeted to the Lysosomal Compartment.

Figure 4:
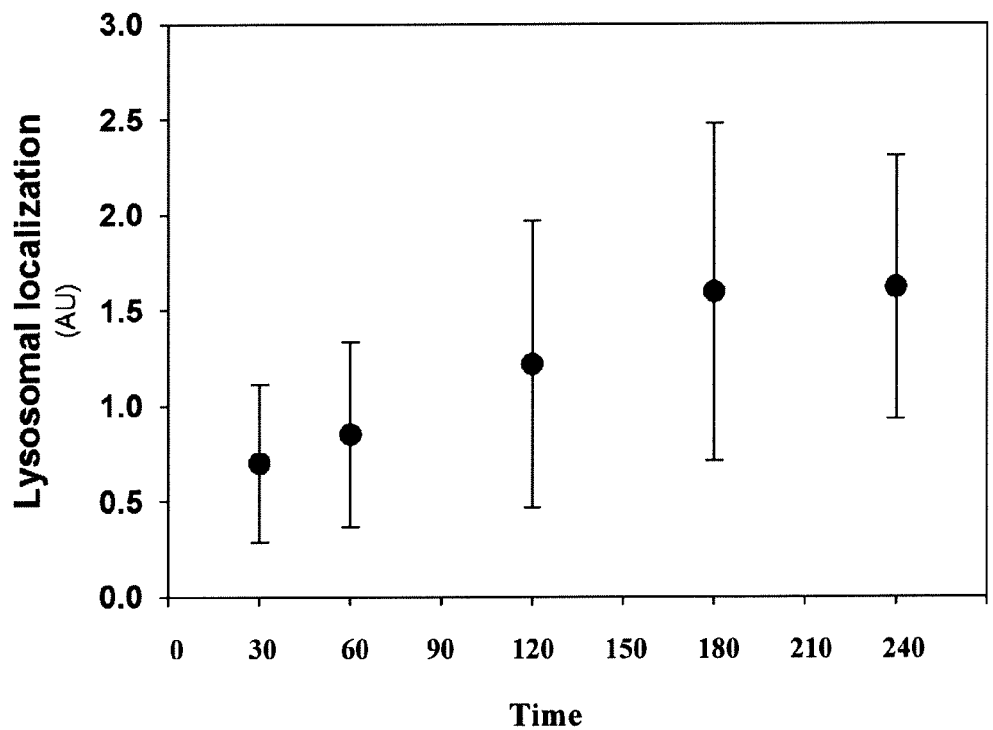
FIG. 4 FAP is sorted to lysosomes. T24 cells were treated with the lysosomal inhibitor leupeptin and allowed to internalize FAP clustered with anti-FAP antibodies for 3 h. Co-localization between FAP and the lysosomal marker Lamp2 was revealed by immunofluorescence, and the percentage of FAP puncta co-localizing with Lamp2 was quantified. Approximately 200 puncta per cell were counted in 6 different cells. In order to estimate the probability of random co-localization, the image corresponding to the FAP channel was rotated 180° and random signal overlap was assessed.

Next, we investigated the post-internalization fate of FAP. Specifically, we tested whether FAP was targeted to the lysosomal compartment following antibody-induced micro-aggregation in the absence of Rab5$^{Q79L}$-GFP expression. This was evaluated by assessing the extent of FAP colocalization with Lysosomal-Associated Membrane Protein 2 (Lamp2) in T24 cells pre-incubated with leupeptin to inhibit lysosomal degradation. Our results showed that FAP colocalized with Lamp2 and that maximal lysosomal accumulation occurred with an approximately 60 min delay as compared to the internalization rate (FIG. 4).

Since integrin complexes are known to recycle back to the plasma membrane, we also evaluated the contribution of different recycling pathways to the intracellular trafficking of FAP. Specifically, we quantified the intracellular accumulation of FAP upon overexpression of the dominant negative mutants of the GTPases that control different recycling pathways. Dominant negative versions of Rab4 or Rab11 did not exert any discernible effect on internalized FAP accumulation. Expression of ARF6 dominant negative mutant only produced very subtle effects on FAP trafficking (data not shown). Taken together, our data indicate that internalized FAP was mainly targeted to the lysosome with a negligible recycling component.

Multivalent Liposomes Undergo FAP-Mediated Internalization in T24 Bladder Tumor Cells.

Figure 5:
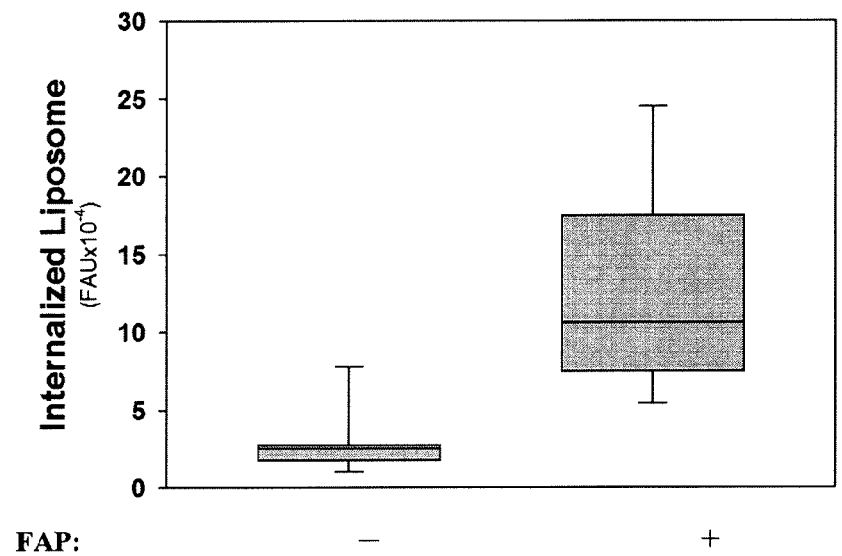
FIG. 5 is a box-plot showing the FAP-mediated internalization of liposomes. T24 cells expressing Rab5$^{Q79L}$-GFP were incubated in the presence (+) or absence (−) of purified FAP for 1 h at 37° C. Then coverslips were rinsed and labeled with Ni$^{2−}$:trisNTA-CF633-liposomes at 10° C. and shifted to 37° C. for 3 h. Internalized CF633-liposomes present in enlarged endosomes were observed and quantified, with the results represented as box-plots in FIG. 5.

Since our results indicate that antibody-induced micro-aggregation substantially accelerated the uptake of FAP in bladder-like, serum-free conditions, we hypothesized that other FAP-FBN-integrin crosslinking strategies would also enhance FAP internalization. Therefore, we next tried a 50 nm-liposome suspension bearing multiple Ni$^{2+}$NTA His$_6$-binding sites per nanoparticle as FAP-FBN-integrin crosslinker instead of antibody. Our results indicate that multivalent Ni$^{2+}$NTA-liposomes, were internalized in the presence, but not in the absence of recombinant purified FAP (FIG. 5). Further these results strongly support the suitability of FAP as targeting agent for nano-carrier based approaches to bladder cancer.

Discussion

This study establishes for the first time the endocytosis mechanism and intracellular route of the FAP (fibronectin attachment protein from *Bacillus Calmette*-Guerin) in bladder tumor cells. Importantly, we developed a strategy to accelerate the uptake of FAP in serum-free environments (such as the lumen of the bladder) and demonstrated its suitability to induce liposome internalization in bladder tumor cells. Overall, the data indicate that FAP is a suitable targeting agent for bladder cancer.

Recombinant purified FAP and an antibody-induced micro-aggregation strategy was used to promote faster FAP internalization by T24 bladder tumor cells. In addition, we relied on the expression of Rab5$^{Q79L}$-GFP fusion protein to accumulate FAP in easy to identify enlarged endosomal compartments. This study shows that FAP can be used to successfully address two important challenges for bladder cancer therapeutics:

1. The presence of an unfavorable extracellular environment: low pH (<6), mechanical stress (filling and voiding cycles) and constant dilution of the lumen content.
2. The relative stasis of bladder cells toward internalizing lumen material.

FAP as a Targeting Agent for Tumor Bladder Cells.

The results demonstrate that purified FAP can surmount the first challenge through high affinity targeting of bladder tumor cells. Specifically, purified His$_6$-FAP recognized FBN fibrils and, as expected, was found to co-localize with activated (i.e., ligand-bound) integrins as revealed by immunofluorescence with an anti-activated integrin antibody. The resulting FAP-FBN-integrin complexes were resistant to low pH conditions that are characteristic of urine and to the ionic strength conditions imposed by our buffer of choice for intravesical instillations (FIG. 6).

Also, we speculate that FAP targeting of bladder tumor cells is superior to other targeting ligands because it binds to FBN-integrin complexes rather than targeting low abundance free integrins or attempting to compete off integrin ligands that are already engaged in FBN complexes. In fact, pre-incubation of FAP with FBN did not increase FAP uptake; rather, it enhanced FAP binding to fibrilar FBN, suggesting that the availability of free integrins was rather limited. Importantly, in addition to its targeting activity, FAP is uniquely advantageous because it is capable of eliciting the immune responses that are thought to play an important role in BCG's therapeutic mechanism.

FAP Internalization.

Since the results demonstrate that purified FAP was internalized by bladder tumor cells, it was anticipated that it may be a suitable reagent for the development of intracellular delivery strategies for cytotoxic cargo. In view of this, a micro-aggregation-based approach was developed to overcome the slow endocytic kinetics of T24 bladder tumor cells. The findings of this study established the importance of multivalency as a clear determinant for controlling FAP endocytosis. In fact, either polyclonal anti-FAP antibodies or multivalent Ni$^{2+}$NTA-liposomes were capable of undergo endocytosis upon FAP binding.

Since most of FAP-FBN fibrils appeared too stable to engage in antibody-induced internalization, FAP endocytosis appears to be associated with FBN-integrin pools that are either not integrated into fibrilar structures or that are destined for turnover. Interestingly, the FAP internalization mechanism reported in this study is similar to that previously described for of FBN turnover in fibroblasts. Specifically, our results suggest a caveolae-dependent mechanism for FAP internalization, with intracellular routing of the complexes to degradative compartments (FIGS. 3-4). These results are also in agreement with a recent report describing the interaction of FBN-integrin complexes with the machinery responsible for protein sorting into late endosomal/lysosomal compartments.

In summary, the data presented herein support the idea that FAP follows the normal FBN-integrin complex trafficking route. The fact that the FAP-FBN-integrin complexes are resistant to pHs lower than those typically found in endosomes is also consistent with this hypothesis.

Interestingly, these results indicate that as opposed to the RhoA-dependent compensatory endocytosis mechanism described in umbrella cells, T24 bladder tumor cells internalize FAP via a different clathrin-independent pathway. We hypothesize that tumor cells may regain common endocytic mechanisms absent or downregulated in the highly differentiated umbrella cells. An alternative possibility is that the FAP micro-aggregation strategy resulted in activation of an endocytic pathway that is not normally used in bladder cells.

CONCLUSIONS

We characterized the association of the BCG fibronectin attachment protein with bladder tumor cells. Further, we established the internalization mechanism and intracellular route of this important therapeutic agent. We also showed the suitability of FAP to be used as targeting agent for bladder tumor cells. In fact, we showed a successful proof-of-principle that FAP can mediate the uptake of artificial liposomes. In addition, this study provides vital information for the design of an efficient strategy for the FAP-based delivery of therapeutics. For example, the kinetics and trafficking results described in this work could be used for the optimization of the composition and fusogenic characteristics of future FAP-nanocarriers.

tein or the functional equivalent thereof, and the cluster induces uptake of the carrier by the patient cell.

6. The method of claim 4 wherein the ligands are antibodies that specifically bind to said non-native peptide tag.

7. The method of claim 4 wherein the carrier comprises a liposome, wherein at least a portion of said plurality of ligands are presented on the external surface of the liposome.

8. The method of claim 7 wherein the diagnostic agent or therapeutic agent is encapsulated within the liposome and the liposome comprises a diameter of 50 nm.

What is claimed is:

1. A method of enhancing targeted uptake of therapeutic or diagnostic agents by a patient's cells, said method comprising the steps of:

providing a multivalent complex comprising at least one carrier and a plurality of fibronectin attachment proteins or functional equivalents thereof attached to the carrier such that each fibronectin attachment protein or functional equivalent thereof is positioned within submicrons of at least one other fibronectin attachment protein or functional equivalent to form a cluster and wherein said complex is linked to a therapeutic or diagnostic agent; and administering said complex to said patient;

wherein upon contact between receptors of a patient cell and the fibronectin attachment proteins or functional equivalents thereof of the complex, the cluster further comprises the receptors of the patient cell.

2. The method of claim 1 wherein:

the multivalent complex further comprises multiple ligands, each ligand bound to a fibronectin attachment protein or the function equivalent thereof and held less than 150 nm apart from each other; and the fibronectin attachment proteins or functional equivalents within the cluster are attached to the carrier through a linker.

3. The method of claim 2 wherein the therapeutic of diagnostic agent is targeted to bladder cancer cells and said administering step comprises introducing said complex into the lumen of the patient's bladder.

4. The method of claim 2 wherein each said fibronectin attachment protein or functional equivalent is a recombinant fusion peptide comprising a non-native peptide tag, and said ligands bind to said non-native peptide tag.

5. The method of claim 2 wherein the ligands are antibodies that specifically bind to fibronectin attachment pro- 9. The method of claim 7 wherein the fibronectin attachment protein or functional equivalent thereof comprises a histidine peptide tag and the ligand is a Ni2+NTA-bearing liposome.

10. The method of claim 3 wherein said fibronectin attachment protein or functional equivalent thereof comprises the RWFV sequence (residues 213-216) of the native peptide.

11. A method of enhancing the targeted uptake of therapeutic or diagnostic agents by a patient's bladder cells, said method comprising the steps of providing a complex that comprises:
a plurality of recombinant fusion peptides, each peptide comprising a fibronectin attachment protein and a non-native peptide tag;
a plurality of ligands bound to said recombinant fusion peptides;
a nanoparticle or nano-carrier wherein said ligands are linked to said nanoparticle or nano-carrier surface and spaced less than 150 nm apart from each other such that each fibronectin attachment protein is positioned within submicrons of at least one other fibronectin attachment protein of the complex to form a cluster; and
a therapeutic or diagnostic agent linked to said ligand or peptide; and contacting said cells with said complex.

12. The method of claim 11 wherein said ligands are antibodies specific for said non-native peptide tag and said therapeutic or diagnostic agent is linked to the constant domain of the antibodies.

13. The method of claim 11 wherein the therapeutic or diagnostic agent is targeted to bladder cancer cells and said contacting step comprises introducing said complex into the lumen of the patient's bladder.

14. A method for enhancing selective uptake of diagnostic or therapeutic agents by a patient's bladder tumor cells comprising the steps of:

providing a stable multivalent complex of fibronectin attachment proteins, wherein the fibronectin attachment protein complex comprises at least one carrier, a plurality of fibronectin attachment proteins attached to the carrier, and a plurality of ligands that bind to fibronectin attachment protein and position at least two fibronectin attachment proteins within submicrons of each other to form a cluster, and wherein said complex is linked to a therapeutic or diagnostic agent; and contacting said bladder tumor cells with said complex;

wherein upon contact between receptors of a bladder tumor cell and the fibronectin attachment proteins of the complex, the cluster further comprises the receptors of the bladder tumor cell.

15. The method of claim 14 wherein said fibronectin attachment protein is a recombinant fusion peptide comprising a non-native peptide tag, and said ligands bind to said non-native peptide tag.

16. The method of claim 14 wherein the ligands are antibodies that specifically bind to fibronectin attachment protein and the cluster induces uptake of the carrier by the patient cell.

17. The method of claim 15 wherein the ligands are antibodies that specifically bind to said non-native peptide tag.

18. The method of claim 14 wherein said ligands are held less than 150 nm apart from each other and the fibronectin attachment proteins within the cluster are covalently attached to one another through a linker.

19. The method of claim 14 wherein said contacting step comprises introducing said complex into the lumen of the patient's bladder.

20. The method of claim 16 wherein the multivalent complex is formed by providing the antibodies at a fibronectin attachment proteins or functional equivalents thereof to antibodies dilution ratio of between 1:600 and 1:1800 to facilitate formation of the cluster.

* * * * *

UNITED STATES PATENT AND TRADEMARK OFFICE
CERTIFICATE OF CORRECTION

Page 1 of 1

PATENT NO.         : 9,518,114 B2
APPLICATION NO.    : 13/884427
DATED              : December 13, 2016
INVENTOR(S)        : Aguilar et al.

It is certified that error appears in the above-identified patent and that said Letters Patent is hereby corrected as shown below:

In the Specification

Column 1, in between Lines 14 and 15, the following header and paragraph should be inserted:
--STATEMENT REGARDING FEDERALLY SPONSORED RESEARCH
This invention was made with government support under CA151961 awarded by the National Institute of Health. The United States Government has certain rights in the invention.--

Signed and Sealed this
Fifth Day of September, 2017

Joseph Matal
*Performing the Functions and Duties of the*
*Under Secretary of Commerce for Intellectual Property and*
*Director of the United States Patent and Trademark Office*